United States Patent [19]
Black et al.

[11] Patent Number: 5,681,437
[45] Date of Patent: Oct. 28, 1997

[54] SAMPLE DEPOSITION DEVICE

[75] Inventors: Jeffrey A. Black, Clinton; Vincent J. Greczanik, Akron; Michael E. Jackson, Fairlawn, all of Ohio

[73] Assignee: Isolab, Inc., Norton, Ohio

[21] Appl. No.: 550,746

[22] Filed: Oct. 31, 1995

[51] Int. Cl.⁶ .................. G01N 27/447; G01N 1/10; B67D 5/02; B01L 11/00
[52] U.S. Cl. .................. 204/456; 204/466; 204/606; 204/616; 222/187; 422/56; 422/99; 422/100; 436/180; 73/61.54
[58] Field of Search .................. 436/180; 422/99, 422/100, 104, 56; 73/61.54; 204/456, 466, 467, 606, 616, 618, 619, 620; 222/187

[56] References Cited

U.S. PATENT DOCUMENTS

| | | | |
|---|---|---|---|
| 3,482,943 | 12/1969 | Csizmas et al. | 204/616 X |
| 3,776,184 | 12/1973 | Harrison | 118/243 |
| 3,839,183 | 10/1974 | Klein et al. | 204/606 |
| 3,855,846 | 12/1974 | Forget et al. | 73/61.54 |
| 4,199,428 | 4/1980 | Hayashi et al. | 204/641 |
| 4,308,822 | 1/1982 | Hijikata et al. | 118/665 |
| 4,328,184 | 5/1982 | Kondo | 422/58 |
| 4,334,879 | 6/1982 | Fujimori | 436/174 |
| 4,351,800 | 9/1982 | Kopp et al. | 422/70 |
| 4,420,353 | 12/1983 | Levine | 156/227 |
| 4,438,205 | 3/1984 | Saint-Leger et al. | 436/71 |
| 4,526,753 | 7/1985 | Boger et al. | 422/56 |
| 4,578,169 | 3/1986 | Vicario et al. | 204/641 |
| 4,622,207 | 11/1986 | Wang | 422/56 |
| 4,776,904 | 10/1988 | Charlton et al. | 156/73.1 |
| 4,803,170 | 2/1989 | Stanton et al. | 436/518 |
| 5,011,779 | 4/1991 | Maimon | 435/293 |
| 5,079,170 | 1/1992 | Rosman et al. | 436/178 |
| 5,413,761 | 5/1995 | Dulaney | 422/56 |
| 5,464,515 | 11/1995 | Bellon | 204/466 |

*Primary Examiner*—Kathryn L. Gorgos
*Assistant Examiner*—John S. Starsiak, Jr.
*Attorney, Agent, or Firm*—Standley & Gilcrest

[57] ABSTRACT

The present invention is a sample deposition device for depositing a plurality of samples onto a test media substrate, and a method of depositing a plurality of samples onto a planar test media substrate, such as a stationary phase chromatographic medium, agar or tissue. In broadest terms, the device of the present invention comprises (a) a substantially planar support portion defining a plane; and (b) an array of substantially planar absorbent portions permanently connected to the support portion, the absorbent portions aligned substantially parallel to said plane. The absorbent portions may be impregnated with a test sample before use. The present invention also includes a method of depositing one or more samples onto a test media substrate.

5 Claims, 4 Drawing Sheets

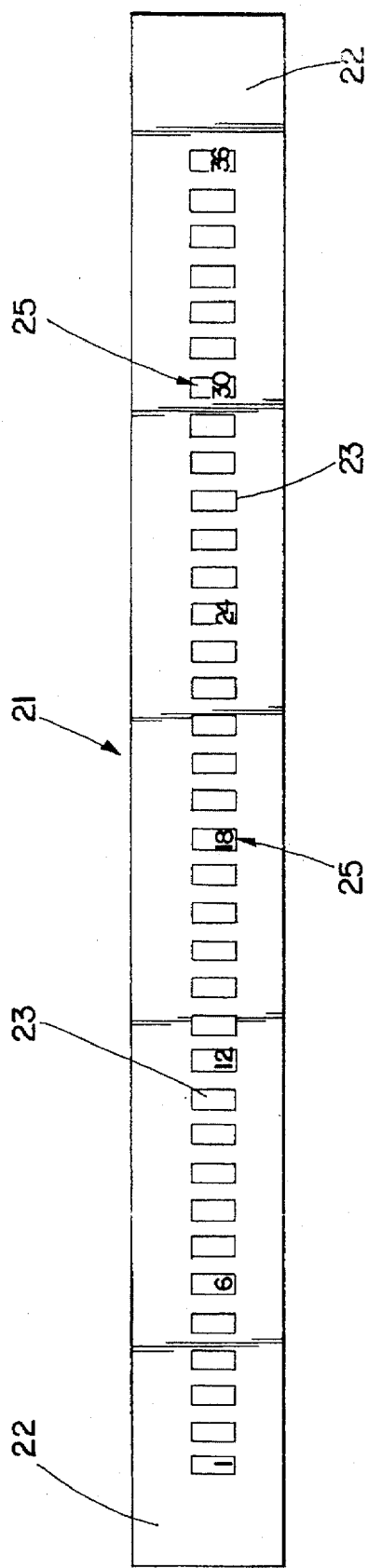
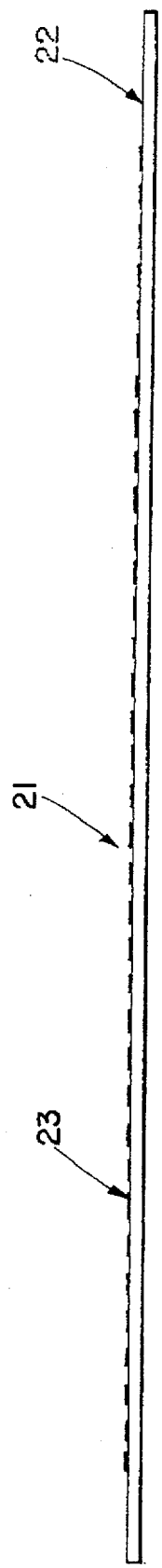
Fig. 4
Fig. 4a

SAMPLE DEPOSITION DEVICE

TECHNICAL FIELD

The present invention is in the fields of biology, biochemistry and analytical chemistry, particularly pertaining to the deposition of samples onto planar solid phase media, such as those used in chromatographic techniques, electrophoresis or thin layer chromatography and the like; or onto planar growth media, such as agar or tissue.

BACKGROUND

One of the important features of any analytical method, particularly in wet chemistry methods, is the handling and deposition of liquids, such as those containing sample or controls to be analyzed.

Examples of techniques where sample handling and deposition are particularly difficult are electrophoresis (including isoelectric focusing) or thin layer chromatography. These techniques often involve the deposition of small volume liquid samples onto the solid phase media used in these chromatographic methods. Because sample amount/volume is typically limited (such as in biochemical assays in the medical, research and forensic fields), it is necessary to assure that samples are preserved and kept from cross-contamination. Therefore, it is desirable to be able to deposit samples on a stationary phase quickly, cleanly, automatically and without contact with potential contaminants such as human touch or other samples.

In the use of the planar media techniques it is at the same time desirable to fully utilize the solid phase area, such as the area of an electrophoretic or thin layer chromatographic gel. Accordingly, it is desirable to be able to deposit a number of samples on a stationary phase of a chromatographic medium while reducing the possibility of contamination from other samples.

It is also desirable to be able to deposit samples onto a stationary phase of a chromatographic medium through any manual or automatic means, such as through the use of automatic dispensing equipment or multi-channel pipettes. However, the use of such equipment generally requires the deposition of samples in a regular array onto the stationary phase media.

One method for introducing samples into the stationary phase employs plastic strips (a. k. a. templates; typically polyester or silicon) containing a regular array of small holes. The template is placed on the solid phase, and the liquid samples added to the wells formed by the holes allowing the liquid samples to come into contact with the solid phase (such as a gel). The liquid may then pass from the well into the solid phase. However, there is a significant problem with cross contamination of adjacent samples with the technique. While passing into the solid phase the liquid may run under the template and contaminate the next well.

Accordingly, it is desirable to produce an apparatus that allows for the clean deposition of samples onto a stationary phase media (e.g., a gel or other stationary phase media) which may be used with automatic dispensing equipment and which better reduces the possibility of cross-zone contamination between samples deposited next to one another. It is also desirable to produce such an apparatus using relatively inexpensive and sterilizable materials.

In view of the present disclosure or through practice of the present invention, other advantages may become apparent.

SUMMARY OF THE INVENTION

The present invention includes a sample deposition device for depositing a plurality of samples onto a test media substrate, and a method of depositing a plurality of samples onto a planar test media substrate, such as a stationary phase chromatographic medium, agar or tissue.

A first embodiment of the device of the present invention (exemplified by FIGS. 1 and 2 herein) comprises (a) a substantially planar support portion defining a support plane; and (b) an array of substantially planar absorbent portions defining a portion plane and releasably connected to the support portion, the absorbent portions aligned substantially parallel to the support plane. The support portion may be of the same or different material as the absorbent portions; the support portion need not be absorbent as it is principally for the positioning of the planar absorbent portions. The support portion typically will be made as a single piece.

More particularly, the sample deposition device of the present invention comprises a substantially planar absorbent material which has been cut so as to form (a) a substantially planar support portion defining a support plane; (b) an array of substantially planar absorbent portions defining a portion plane and releasably connected to said support portion, the absorbent portions aligned substantially parallel to that plane. In such embodiments the device is prepared by cutting it from a single piece of absorbent material. The sample deposition device of the present invention may be produced by any technique known in the art, such as by laser cutting techniques and die cutting techniques. Laser cutting techniques are preferred.

A second embodiment of the device of the present invention (exemplified by FIGS. 4 and 4a herein) comprises (a) a substantially planar support portion defining a plane; and (b) an array of substantially planar absorbent portions permanently connected to the support portion, the absorbent portions aligned substantially parallel to said plane. An example of this embodiment may be the attachment of an array of substantially planar absorbent pieces to a solid support (such as a plastic backing) by an adhesive for example.

The support and/or absorbent portions may be marked with identifying indicia, such as numbers, letters and/or words, by printing or by die-cutting or laser marking.

The present invention in all its embodiments is not limited to the number, size, shape or arrangement of the absorbent portions.

Preferably, the absorbent portions of the sample deposition device of the present invention are made of an absorbent paper, such as cotton linter paper, wetable polymeric materials or matted fibrous materials, such as a glass fiber matting or paper. in this regard, one of the advantages of the use of fibrous materials (or materials of similar filtering capability) is that the liquid samples still containing particulate material are subjected to a final filtering before encountering the test media, in the case of dispensing of the sample onto the absorbent portions already positioned on the test media substrate. Instances where such an advantage may be important is in the testing of blood samples or ground organic material, such as plant seeds.

The sample deposition device of the first embodiment of the present invention (the embodiment using releasable absorbent pieces) may be cut using any appropriate cutting technique such as laser cutting techniques and die cutting techniques; laser cutting techniques being most preferred. It is also preferred that the absorbent material is cut so as to leave at least one breakable connection between the support portion and each of said absorbent portions. Most preferably, absorbent material is cut so as to leave at least two breakable connection between that support portion and each of the absorbent portions.

The breakable connection(s) between the support portion and each of the absorbent portions should be sufficiently thin so as to be breakable upon the sample deposition device first being placed upon the test media substrate (typically a stationary phase chromatographic media, electrophoretic media or agar) followed by the support portion being separated from the test media substrate by breaking of the connection(s). The thickness of the breakable connection(s) (such as filaments or paper portions) may be varied in order to provide for the appropriate tear force to correspond to the desired force of separation from the test media substrate. This tear force may vary according to several factors such as the nature (such as weight, flexibility and tensile strength) and thickness of the connection material, the wetness and wetability of the connection material and the wetness of the test media substrate (such as where the connections are paper or wetable fiber and become weakened upon wetting) and its tackiness, if any (such as through surface tension, etc.). Generally, the thickness may be determined without undue experimentation, in light of the present disclosure.

The test media substrates for which the device of the invention may be used to apply samples may include electrophoresis gels, thin layer chromatography gels, agar plates, organic tissue (living or dead), paper chromatography slides, etc. For instance, the device of the present invention may be used to place organic, inorganic or biochemical samples on gels for electrophoresis, isoelectric focusing gels or other types of thin layer chromatography media; for the application of biochemical materials, microorganisms, and like substances to agar plates; for the application of materials to organic tissue such as for scientific purposes, such as in the application of antigenic materials for sensitivity studies. In some instances, the desired test media substrate may be wetted or otherwise supplied with an inert substance in order to render the test media substrate tacky or sticky to the absorbent portions of the device.

As used herein, the term "samples" may refer to any substance that may be deposited using a device of the present invention. Such substances may be of almost any type of liquid and/or liquid-borne or liquid-solvated substance. Such substances may include water, organic liquids, or aqueous or organic solutions or suspensions of one or more substances. Examples or organic liquids which may be used as solvents include tetrahydrofuran, dimethyl sulfoxide, DMF, etc. These substances may include whole or lyophilized blood, plasma, dyes, organic chemicals, inorganic chemicals, biochemicals, proteins, carbohydrates, nucleotides, peptides, etc. These materials may include control materials prepared for comparative testing. Accordingly, reference herein to samples may refer to a number of samples which are the same, similar or different with respect to chemical nature and/or concentration.

The device of the present invention may be pre-impregnated with any one or more of such substances. For instance, the absorbent portions of the device may be pre-impregnated with a series of controls of different or the same substances which may be of a variety of concentrations, such as in a series of increasing concentrations. These substances may be dried or lyophilized, and then rewetted prior to use in the analytic or scientific technique.

The absorbent material used in the present invention may be cut so as to leave at least one breakable connection between the support portion and each of the absorbent portions. In the case of linter paper, the one breakable connection(s) typically will be of a thickness in the range of 0.1 mm to 1.5 mm, preferably 0.3 mm to 0.7 mm, and most preferably 0.3 mm, where application of the sample is intended to be placed onto an electrophoretic gel. With the guidance of the present disclosure and without undue experimentation, the appropriate thickness for the desired test media substrate can be determined.

The presently preferred arrangement of the absorbent portions in the device of the present invention are where the absorbent material is cut so as to form a channel in the support portion and so that the array of absorbent portions is aligned in the channel with at least two breakable connections between the support portion and each of the absorbent portions. It is also preferred that the absorbent portions are arranged in a regularly spaced array where the device is to be used with multichannel pipettes such as those used in liquid handling equipment, although any other manual or automatic dispensing device may be used, such as liquid droppers or single-channel pipettes.

For storage, transport and protection during test media substrate application, the sample deposition devices of the present invention may be provided with a releasable cover of a polymeric material to protect the device from damage or contamination. Such a protective cover may be attached with a releasable adhesive, preferably attached only to the support portion of the device so as not to detach the absorbent portions prematurely.

The present invention also includes a method of depositing a plurality of samples onto a substantially planar test media substrate using a device of the first embodiment of the present invention. The method involves the steps of: (a) obtaining a substantially planar test media substrate; (b) placing onto the substantially planar test media substrate a sample deposition device having releasable absorbent pieces as described in the first embodiment described above; (c) separating said support portion from said absorbent portions; and (d) depositing each of said plurality of samples onto respective said absorbent portions. The method may be performed by depositing the plurality of samples onto the absorbent portions by any method, such as an by automatic sample dispenser or multi-channel pipette.

The present invention also includes another method of depositing a plurality of samples onto a substantially planar test media substrate using a device of the first embodiment of the present invention wherein the absorbent portions are pre-impregnated. This method involves the steps of: (a) obtaining a substantially planar test media substrate; (b) placing onto the substantially planar test media substrate a sample deposition device having releasable, pre-impregnated absorbent pieces as described in the first embodiment described above.

The present invention also includes another method of depositing a plurality of samples onto a substantially planar test media substrate using a device of the second embodiment of the present invention wherein the absorbent portions are pre-impregnated. This method involves the steps of: (a) obtaining a substantially planar test media substrate; (b) placing onto the substantially planar test media substrate a sample deposition device having permanently attached, pre-impregnated absorbent pieces as described in the first embodiment described above.

The present invention naturally also involves analytical and experimental methods that include the additional steps necessary to perform the test or experimentation to which the present invention pertains, such as allowing the samples to migrate on the electrophoretic gel or thin layer chromatography gel, followed by measuring the presence and/or amount of the sample(s) on the gel. In the case of biological testing and experimentation involving methods using tissue or agar, this may involve the required steps such as allowing a microorganism to grow on an agar surface or allowing a tissue to react to a substance, followed by measuring the degree of growth or inhibition of growth, or the reaction of the tissue to the substance(s).

BRIEF DESCRIPTION OF THE DRAWINGS

FIG. 4 is a plan view of a sample deposition device in accordance with yet another embodiment of the present invention; and FIG. 4a is an elevational view of a sample deposition device in accordance with the embodiment of the present invention shown in FIG. 4.

DETAILED DESCRIPTION OF THE PREFERRED EMBODIMENTS

In accordance with foregoing summary, the following represents what is considered to be the best mode of the device and method of the present invention as applied to the deposition of an aqueous sample onto an electrophoresis gel.

Figure 1:
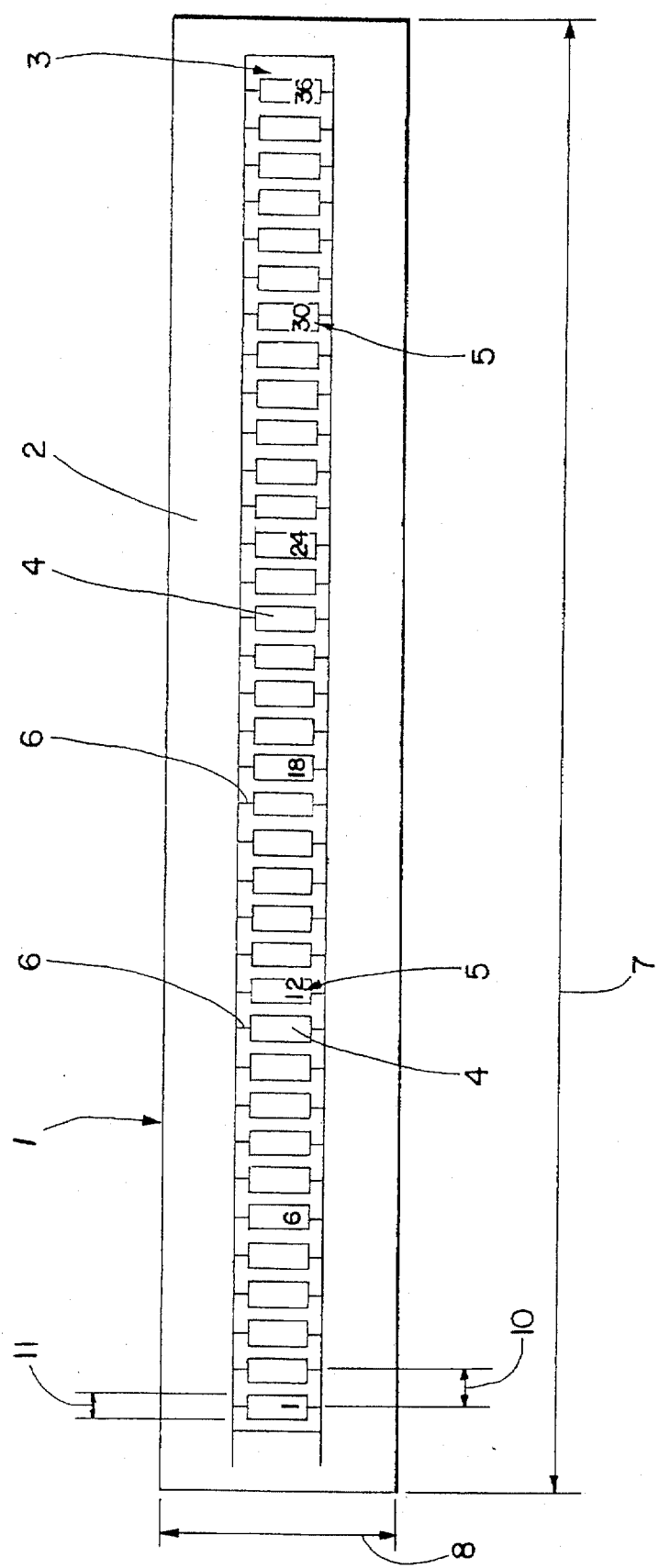
FIG. 1 is a plan view of a sample deposition device in accordance with one embodiment of the present invention.

FIG. 1 shows sample deposition device 1 laser cut from a single piece of linter paper and made up of support portion 2 having channel 3. The device also has thirty-six (36) absorbent portions 4 which are provided with laser etched numerals 5. The breakable portions 6, having a thickness of 0.3 mm, connect the absorbent portions 4 to support portion 2.

The dimensions shown in FIG. 1 are as follows: dimension 7=241 mm, dimension 8=23 mm, dimension 9=7.0 mm, dimension 10=5.771 mm (on center), and dimension 11=4.0 mm.

Due to the fragile nature of the breakable portions, it is preferred that the devices be stored and shipped between solid support sheets, such as might be made from sheets of relatively stiff paper.

Figure 2:
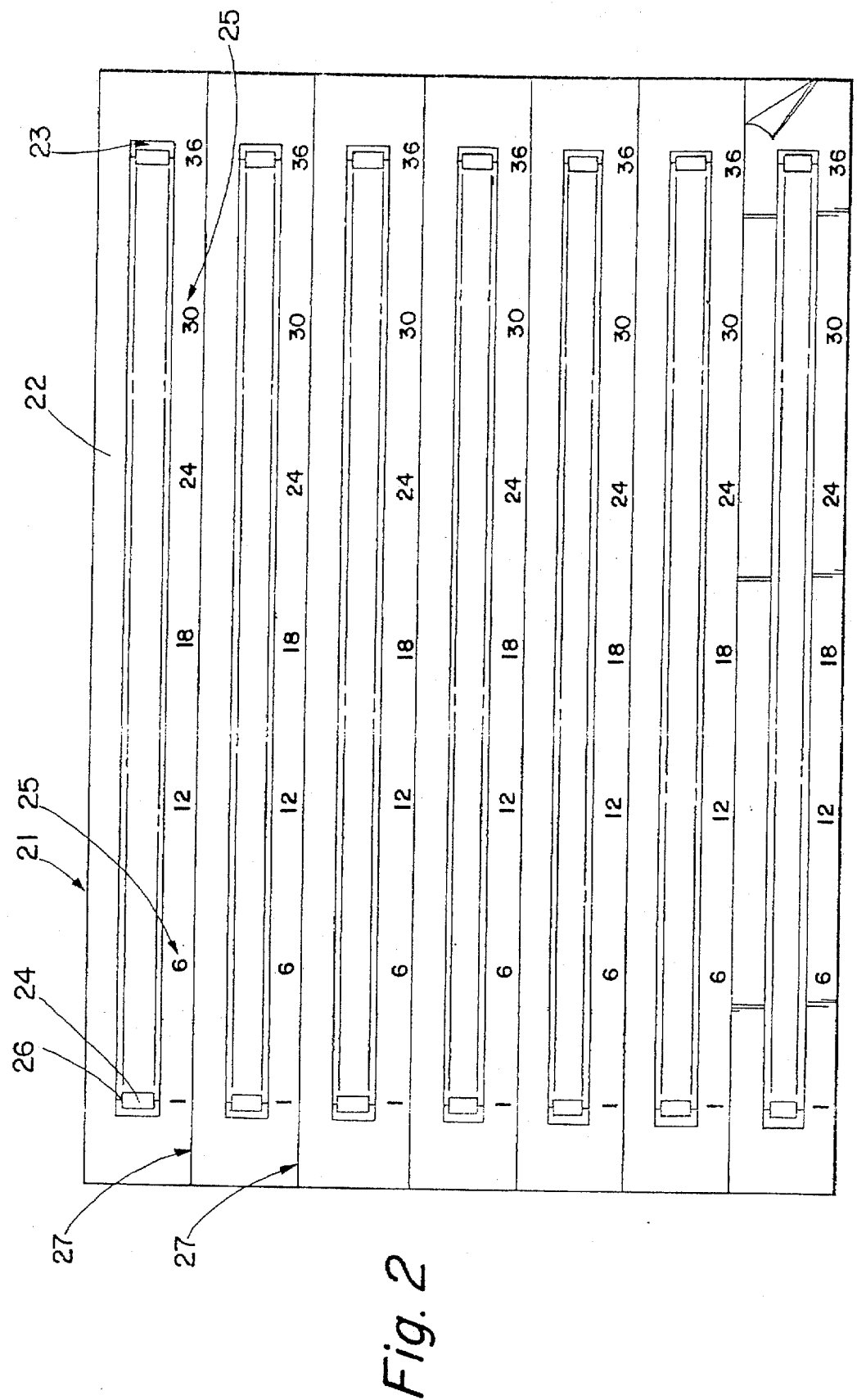
FIG. 2 is a plan view of a sample deposition device in accordance with another embodiment of the present invention.

FIG. 2 shows an alternative embodiment of the present invention, with the sample deposition device shown as a series of seven (7) such devices. FIG. 2 shows sample deposition device 21 laser cut from a single piece of linter paper and made up of support portion 22 having channel 23 and being provided with laser etched numerals 25. The device also has thirty-six (36) absorbent portions 24. The breakable portions 26, having a thickness of 0.3 mm, connect the absorbent portions 24 to support portion 22. FIG. 2 also shows releasable polymeric cover as applied to one of the seven sample deposition devices.

FIG. 2 shows that the sample deposition device of the present invention may be produced as a series of devices (i.e., seven (7) linear devices) cut from a single piece of paper, and separable by a perforation or scorings 27.

The dimensions of the sample deposition device 27 may be the same as those of sample deposition device 1 shown in FIG. 1.

Figure 3:
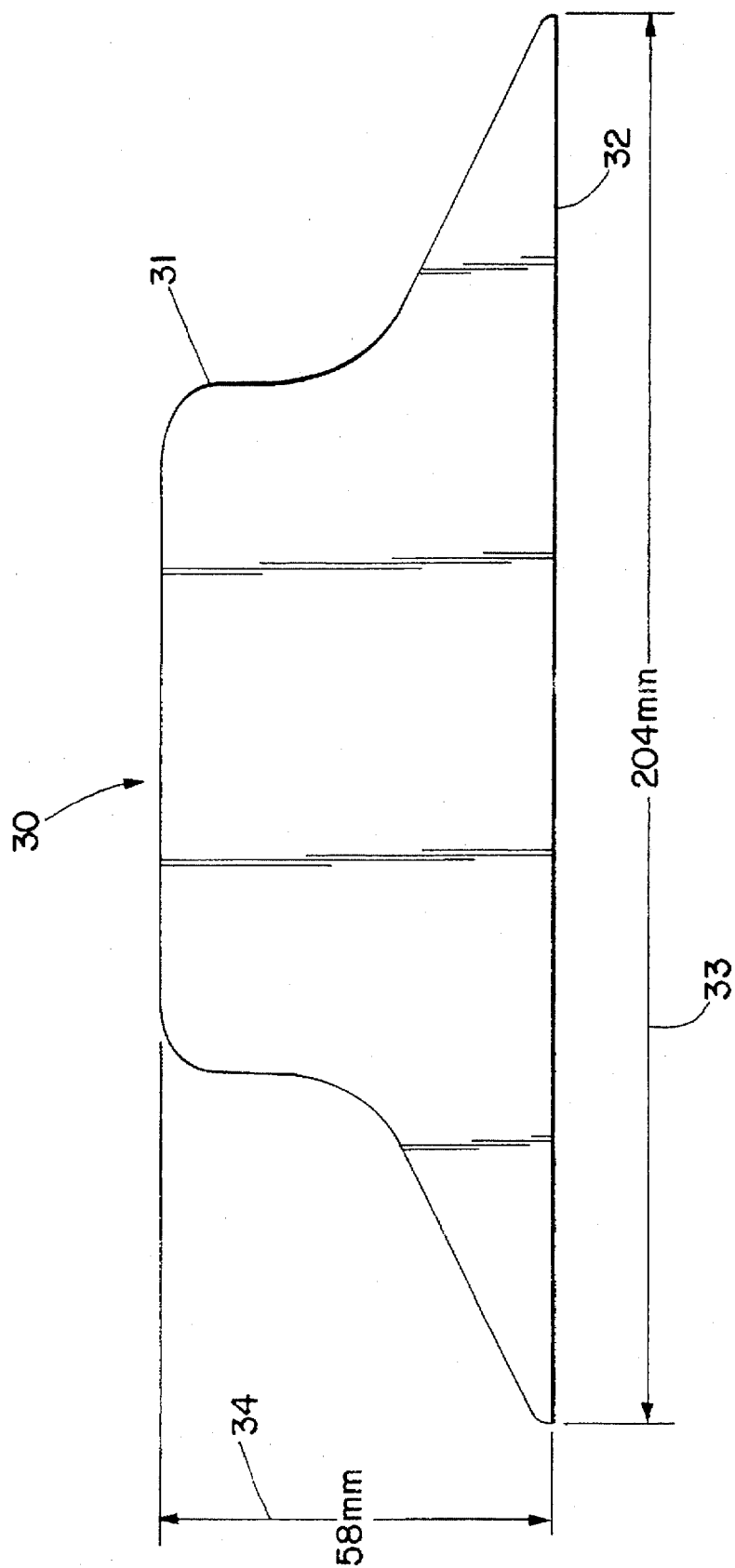
FIG. 3 is an elevational view of a hand tool used in accordance with the device and method of the present invention.

To use the device of the present invention in an electrophoretic method, an electrophoresis gel is prepared and a sampling device as described herein placed onto the gel. The absorbent portions are placed in contact with the gel so that they slightly adhere to the gel. In some instances it may be preferable to urge the absorbent portions into intimate contact with the gel such as with a sterile tool or a gloved finger. An example of such a tool is shown in FIG. 3. FIG. 3 shows tool 30 having handle portion 31 and blade portion 32. Blade portion preferably should be of a length approximately equal to that of the length of the array of the absorbent portions so that the operator can tamp the absorbent portions evenly onto the test media substrate surface. Dimension 33 of the blade is about 204 mm and dimension 34 is about 58 mm. Tool 30 may be of an acrylic material of about 0.25 inch thickness. The tool is used by placing its blade along the absorbent potions to help in separating them without dislodging or disorienting them, while holding the array of absorbent portions onto the test media substrate surface with the tool of FIG. 3.

The support portion is then separated from the absorbent portions, usually by pulling the support portion from the surface of the gel.

The samples, if not already impregnated into the absorbent portions, are then placed onto respective absorbent portions. It is preferred that the samples are deposited onto the absorbent portions by an automatic sample dispenser or multichannel pipette. This is made easiest where the absorbent portions are in a regularly spaced array to allow the dispenser to be programmed, or for easier use of a multichannel pipette where the spacing matches that of the pipette tip spacing.

FIGS. 4 and 4a also show an alternative embodiment of the present invention. FIGS. 4 and 4a show sample deposition device 21 comprising support portion 22 which is a polyester film, and thirty-six (36) absorbent portions 23 of filter paper (i.e., dimensions of 0.118 inch×0.276 inch) which are provided with laser etched numerals 25. The absorbent portions 23 are spaced apart by about a distance of 0.109 inch, and may be permanently attached by any method of attaching an absorbent material to a solid support, such as through the use of adhesives. The absorbent portions may be of any size number or shape. It is preferred that they are arranged in a regular array.

The method of the present invention includes a method for depositing a plurality of samples onto a substantially planar test media substrate, by using a device such as that shown in FIGS. 1 and 2. The method comprises the steps of: (a) obtaining a substantially planar test media substrate; (b) placing onto the test media substrate a sample deposition device in accordance with the present invention; (c) separating the support portion from absorbent portions; and (d) depositing each of the plurality of samples onto respective absorbent portions. The plurality of samples are preferably deposited onto the respective absorbent portions by an automatic sample dispenser known in the art, such as an automatic pipetter.

The present invention also includes a method for depositing a plurality of samples onto a substantially planar test media substrate, by using a device such as that shown in FIGS. 1 and 2. The method comprises the steps of (a) obtaining a substantially planar test media substrate; (b) placing onto the test media substrate a sample deposition device in accordance with the present invention, the absorbent portions being impregnated with a respective sample; and (c) separating the support portion from the absorbent portions.

The present invention also includes a method for depositing a plurality of samples onto a substantially planar test media substrate, by using a device such as that shown in FIGS. 4 and 4a. The method comprises the steps of: (a) obtaining a substantially planar test media substrate; and (b) placing onto the test media substrate a sample deposition device in accordance with the second embodiment of the present invention, the absorbent portions being impregnated with a respective sample.

In view of the foregoing disclosure, it will be within the ability of one of ordinary skill in the relevant art to make alterations to the present invention, such as through the variation of the arrangement of parts and the use of equivalent materials and process steps, without departing from the spirit of the invention as reflected in the appended claims.

What is claimed is:

1. A sample deposition device for depositing a plurality of samples onto a test media substrate, comprising a single piece of a substantially planar cotton linter paper, said single piece of cotton linter paper cut so as to form:

(a) a substantially planar support portion deforming a support plane;
   (b) an array of substantially planar absorbent portions defining a portion plane and permanently connected to said support portion, said array of absorbent portions aligned in the plane of said support plane.

2. A sample deposition device according to claim 1 wherein said absorbent portions are arranged in a regularly spaced array.

3. A sample deposition device according to claim 1 additionally comprising a releasable cover of a polymeric material attached to said device.

4. A method of depositing a plurality of samples onto a substantially planar test media substrate, said method comprising:

(a) obtaining a substantially planar test media substrate; and
   (b) placing onto said substantially planar test media substrate a sample deposition device for depositing a plurality of samples onto a test media substrate, said device comprising a single piece of a substantially planar absorbent material, said single piece of material cut so as to form:
      (i) a substantially planar support portion defining a support plane;
      (ii) an array of substantially planar absorbent portions defining a portion plane and permanently connected to said support portion, said absorbent portions aligned in the plane of said support plane, at least one of said absorbent portions comprising cotton linter paper and being impregnated with at least one of said plurality of samples.

5. A method according to claim 4 wherein said test media substrate is selected from the group consisting of electrophoresis gels, thin layer chromatography media, agar, and organic tissue.

* * * * *